(12) United States Patent
Bassa

(10) Patent No.: US 6,660,309 B2
(45) Date of Patent: Dec. 9, 2003

(54) ANTITUMOR AGENT

(75) Inventor: Babu V. Bassa, San Diego, CA (US)

(73) Assignee: Biozak, Inc., San Jose, CA (US)

(*) Notice: Subject to any disclaimer, the term of this patent is extended or adjusted under 35 U.S.C. 154(b) by 81 days.

(21) Appl. No.: 09/954,723

(22) Filed: Sep. 14, 2001

(65) Prior Publication Data

US 2003/0054054 A1 Mar. 20, 2003

(51) Int. Cl.[7] ............... A61K 35/78; G01N 33/574; C12N 5/00; C12N 5/02
(52) U.S. Cl. ............... 424/769; 424/775; 435/7.23; 435/377
(58) Field of Search ............... 424/769, 775; 435/377, 7.23

(56) References Cited

PUBLICATIONS

Arnold et al., Digestion (2000) 62 Supp.1:84–91.
Augusti, Ind. J. Physiol. Pharmacol. (1975) 19:218–220.
Augusti et al., Ind. J. Med. Res. (1994) 99:82–86.
Babu et al., Ind. J. Biochem. Biophys. (1988) 6:714–718.
Cragg, Ciba Found Symp. (1994) 185:178–196.
Cragg, Seminar Oncol. (1997) 24:156–163.
Daniel et al., Ind. J. Exp. Biol. (1998) 9:902–906.
Del Corral et al., J. Med. Chem. (2001) 44:1257–1267.
Gill et al., Postgrad. Med. J. (1997) 73:640–641.
Jonathan et al., Cur. Opin. Oncol. (2001) 13:52–56.
Kumar et al., Ind. J. Biochem. Biophys. (1989) 26:400–404.
Lee, Med. Res. Rev. (1999) 19:569–596.
Levya et al., Anticancer Res. (2000) 20:1029–1031.
Rougier and Mitry, Digestion (2000) 62:73–78.
Cherian et al., "Antidiabetic Effect of a Glycoside of Pelargonidin Isolated from the Bark of a Ficus bengalensis Linn" Indian J. of Biochemistry and Biophysics 29:380–382 (1992).
Subramanian et al., "Chemical Constitutents of Ficus bengalensis" Indian J. Chem. 15B:762–763 (1977).

Primary Examiner—Christopher R. Tate
Assistant Examiner—Michele C. Flood
(74) Attorney, Agent, or Firm—Morrison & Foerster LLP

(57) ABSTRACT

A composition is obtained from Banyan tree bark that has insulin antisecretory and cytotoxic properties. The composition can be useful in treating conditions characterized by hyperinsulinism including insulinoma and infant hyperinsulinism.

2 Claims, 3 Drawing Sheets

ANTITUMOR AGENT

FIELD OF THE INVENTION

The invention relates to the field of natural products for use in treating tumors, especially pancreatic beta cell tumors, often referred to as insulinomas. More particularly, the invention concerns compounds obtainable from Banyan tree bark which are effective with regard to malignant and benign tumors characterized by pancreatic β cell transformations.

BACKGROUND ART

It is well understood that current therapies designed for the control and treatment of tumors in general, and malignant tumors in particular, are less than satisfactory. The hammer-fisted approaches of surgery, chemotherapy and radiotherapy are clearly unfocused and accompanied by unpleasant, and often quite serious, side effects as well as being characterized by limited effectiveness. Other treatment methods based on natural products are currently in use (Lee, K. H., *Med. Res. Rev.* (1999) 19:569–596) and others are in clinical trials (Levya, A., et al., *Anticancer Res.* (2000) 20:1029–1031). These remedies, while they may be effective in particular instances, can hardly be considered to solve the overall problem.

The present invention provides a plant derived agent which is focused on the treatment of tumors of particular origins, most prominently those which can be characterized as insulinomas. The new derivative is also cytotoxic to additional cell lines which presage its use in treatment of tumors with characteristics analogous to these cell lines. It is not cytotoxic to others, indicating a specificity of effectiveness that is advantageous in designing targeted treatments.

Pancreatic endocrine tumors, in general, secrete excess amounts of hormones and can be classified as insulinomas, gastrinomas, VIPomas, glucagonomas, and somatostatinomas, for example, by virtue of the nature of the hormones they secrete (Jonathan, C., et al., *Cur. Opin. Oncol.* (2001) 13:52–56). Insulinoma is a very common type, although it is more common in small domestic animals than in humans. Insulinomas are characterized by hypoglycemia and hyperinsulinism, and have the consequence of neuroglycopenia in humans. Behavioral changes often accompany these tumors, both in small animals (such as ferrets) and in humans.

Treatment of insulinomas specifically has focused on surgery (although localization is often difficult) and the use of certain compounds, including dizoxide (Gill, G. V., et al., *Postgrad. Med. J.* (1997) 73:640–641); streptozotocin and doxorubicin (Philippe, R., et al., *Digestion* (2000) 62:73–78); and analogs of somatostatin (Arnold, R., et al., *Digestion* (2000) 62 Supp. 1:84–91). An additional herbal medication has been used in ferrets (Bodofsky, D., www.newrainbowbridge.com).

Of particular interest is the use of somatostatin as this compound (a cyclic 14 amino acid peptide) exhibits antiproliferative and antisecretory effects in endocrine tissues. Analogs of somatostatin, such as octreotide and lanrcotide are typical of the redesigned somatostatin compounds currently in use in antitumor treatment. However, as it is known that somatostatin exerts its effects through interaction with G-protein coupled plasma membrane receptors, and such receptors are only present in approximately 50% of insulinomas, the effectiveness of these treatments is limited.

Other compounds of plant origin which are useful in antitumor treatment include dactinomycin, bleomycin, vinblastine, irinotecan, topotecan, etoposide, and paclitaxel. The compounds useful in this regard include a multiplicity of categories, including lectins, polyphenolic compounds, sesquiterpene lactones, alkaloids, polysaccharides, anthracenediones, tannins, lignans, quassinoids, triterpene glucosides, flavanoids, colchicine derivatives, and quinone derivatives (see, for example, Cragg, G. M., *Seminar Oncol.* (1997) 24:156–163; Cragg, G. M., et al., *Ciba Found Symp.* (19994) 185:190–196; Jose, M., et al.,*J. Med. Chem.* (2001) 44:1257–1267.)

A number of compounds have been isolated from the bark of *Ficus bengalensis* (Banyan tree). Isolation of a compound that improves glucose tolerance in alloxan-diabetic rabbits has been reported by the present inventor Babu, B. V., et al., Thesis submitted to University of New Delhi (Dec. 1985); Babu, B. V., et al., *Ind. J. Biochem. Biophys.* (1988) 6:714–718. Two flavanoid glycosides, the 5,3' dimethyl ether of leucocyanidin-3-o-β-galactosyl cellobioside and the 5,7-dimethyl ether of leucopelargonidin-3-o-α-L rhamnoside have been shown to produce hypoglycemic (antidiabetic) affects in experimental animals. See Kumar, R. V., et al., *Ind. J. Biochem. Biophys.* (1989) 26:400–404; Augusti, K. T., *Ind. J. Physiol. Pharmacol.* (1975) 19:218–220; Augusti, K. T., et al.,*Ind. J. Med. Res.* (1994) 99:82–86. Antioxidant effects of these compounds have also been shown in hyperlipidemic rats (Daniel, R. S., et al., *Ind. J. Exp. Biol.* (1998) 9:902–906).

It has now been found that in addition to the compounds of the foregoing effects, a preparation from Banyan bark exhibits insulin antisecretory activity and is cytotoxic to specific target cells.

DISCLOSURE OF THE INVENTION

The invention provides a method to isolate a composition from Banyan bark which exhibits a characteristic spectrum of cytotoxicity with respect to cells important in the development of tumors, especially those of the pancreas and kidney. The isolated composition is useful in treatment of tumors characterized by these cells and in inhibiting the production of insulin.

Thus, in one aspect, the invention is directed to a method to isolate a composition which inhibits insulin secretion in βTC-6 cells and HIT-T15 and is non-cytotoxic to βTC-6 cells and cytotoxic to HIT-T15 cells; is cytotoxic to the non-insulin secretory cell line SV40 Mes13 cells, but not cytotoxic to the non-insulin secretory cell line MDCK cells.

The Method Comprises a) extracting the bark of *Ficus bengalensis* with a solvent of lower alcohols to obtain an extract;

b) drying the extract to obtain a residue;

c) dissolving the residue in methanol;

d) loading the dissolved residue onto an activated silica gel column;

e) eluting the column with additional ethanol:hexane (2:1) to obtain an eluent; and f) removing solvent from the eluent to obtain said composition.

In another aspect, the invention is directed to a composition having the aforesaid characteristics which is obtainable by the method described. In still another aspect, the invention is directed to methods to treat tumors, especially of the pancreas which method comprises administering to a subject in need of such treatment an effective amount of the composition of the described characteristics. In still another aspect, the invention is directed to a method to inhibit insulin secretion using this composition.

MODES OF CARRYING OUT THE INVENTION

Figure 1:
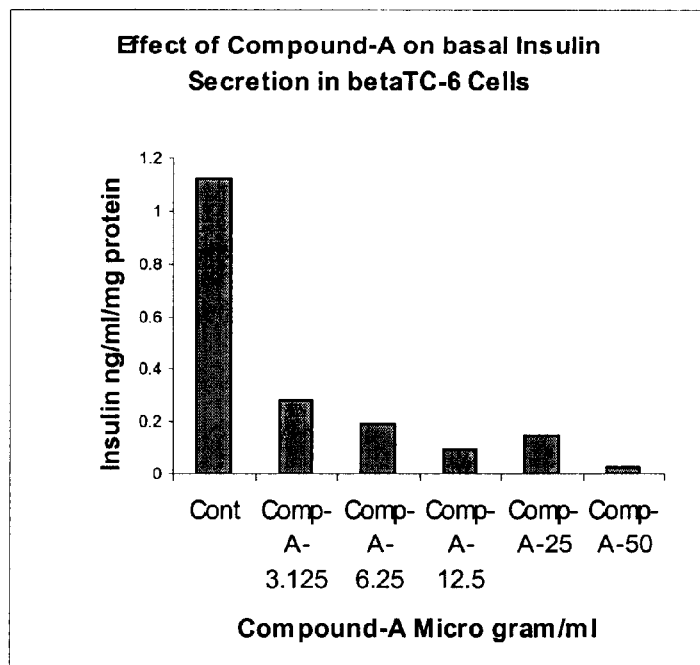
FIG. 1 is a graph showing the effect of Composition A on basal insulin secretion in βTC-6 cells.

The invention provides a composition which has a useful spectrum of activity with regard to cytotoxicity against tumors and is able specifically to treat tumors related to these cell lines in the pancreas. The composition is also useful in decreasing the secretion of insulin and in treating insulinomas.

The composition of the invention is obtainable from the bark of the Banyan tree. The procedure for preparation involves extraction in a polar, ethanolic solvent and isolation from other components using an activated silica column. The extract is dried, dissolved in a minimum of methanol, and placed over a silica gel column which is equilibrated with ethanol:hexane (2:1), a solvent denoted etx-oh. The column is then eluted with etx-oh to obtain an eluent containing Composition A, which then can be dried and redissolved in non-aqueous media such as acetone, ethanol, methanol or dimethyl sulfoxide (DMSO) prior to dilution in buffer for physiological testing and use.

The resulting composition is useful to inhibit insulin secretion whether secreted basally or stimulated by, for example, tolbutamide. Thus, the effects of low insulin secretion in model systems can readily be studied. For example, the effects of decreasing the level of insulin secretion in otherwise normal mice, transgenic mice, or other experimental animal model can be evaluated by administering to the model system the composition of the invention in an amount able to lower the secretion of insulin by the cells endogenous to the animal. Further, the effects of altering insulin secretion in insulin secreting cell lines, such as those illustrated herein, can be evaluated by contacting the cell line with the composition of the invention and observing additional metabolic effects associated with insulin release.

In addition to the use of the composition of the invention as a laboratory tool to study insulin-related metabolism (as opposed to exploring the nature of the biological function of the composition itself) the compositions of the invention can be used to lower insulin levels in subjects who suffer from the effects of overproduction of this hormone. Hyperinsulinism is a common symptom of insulinoma in both humans and animals. Additionally, there is a congenital form of infant hyperinsulinism in which infants suffer from hypoglycemia and elevated ammonium levels. For use in these applications, typically the composition is formulated into pharmaceutical or veterinary compositions for administration to the affected subjects. Pharmaceutical compositions are tailored for the mode of administration and a compendium of such compositions well known to those of ordinary skill is set forth in *Remington's Pharmaceutical Sciences*, latest edition, Mack Publishing Co., Easton, Pa., incorporated herein by reference. Thus, for injection, the composition is formulated in suitable excipients so as to provide osmotic balance; for oral administration the composition may be incorporated into capsules, tablets, syrups, powders and the like; the composition may also be formulated for transdermal or transmucosal administration using skin patches or suppositories. Transmucosal administration may also be intranasal and aerosol formulations are included within the scope of the invention. The composition can also be formulated into liposomes or sustained release compositions. The nature of the formulation will depend on the mode of administration and the nature of the subject.

As noted above, the subjects may be human, but may also be animals, including livestock and domesticated animals, both mammalian and avian.

Pharmaceutical or veterinary compositions of the composition of the invention may also be used for the treatment of tumors which are characterized by the properties of the cell lines for which the composition of the invention is cytotoxic. Thus, tumors which are characterized by the properties of HIT-T15 cells or SV40 Mes 13 cells can be treated using veterinary or pharmaceutical compositions of the invention.

Stimulation of insulin secretion is highly dependent on the activation of L-type calcium channels in pancreatic β bells. Thus, Composition A is considered as an L-type calcium channel blocker. Composition A is thus useful in the treatment of hypertension, as are other calcium channel blockers.

The following examples are intended to illustrate but not to limit the invention.

EXAMPLE 1

Preparation of Composition A

A. Freshly cut bark was obtained from the Gautam Global, Inc., of India and stored at −20° C. until used. The outer chlorophyll layer and the inner wood layer were removed from each piece of the bark using a kitchen knife. The bark was then cut into small pieces, dried and ground in a kitchen grinder. The bark powder was extracted with ethanol (Fisher Scientific, Cat #: A 962$^{F}$-1 GAL; Composition: 90% ethanol, 5% methanol, and 5% isopropanol.). One and half liters of the solvent was used per 100 g of the dried powder. Extraction was carried out at room temperature in 2-liter flask with the help of a magnetic stirrer. The extract was filtered, centrifuged to remove fine debris and evaporated to dryness to obtain a dried residue.

B. Seven grams of activated silica gel (Fisher Scientific, Catlog No: 196724) was suspended in approximately 100 ml of ethanol:hexane (2:1)(etx-oh). The slurry was loaded into a glass column of 1×30 cm dimensions. The column was packed by passing at least 50 ml of etx-oh through it with occasional tapping.

60 mg of the dried residue obtained in paragraph A was dissolved in 0.5 ml of methanol and loaded on the column that is drained of excess solvent. The sample was drained into the silica gel bed, and the top of the column was filled with etx-oh and washed with 100 ml of etx-oh. The first volume of about 50 ml of colorless wash was discarded and the next volume of 50 ml eluent, which had a reddish-yellow color, was collected and evaporated to dryness. This fraction is designated Composition A. Excess solvent on the column was drained off and the column was filled with methanol. Elution was carried out with methanol until almost of all of the material on the column was eluted as indicated by the color. The methanol eluent was evaporated to dryness. This fraction is designated as the methanol fraction. Composition A and the methanol fraction were tested on cell cultures for their effect on insulin secretion and their cytotoxicity.

EXAMPLE 2

Assay of Composition a Effect on Insulin Secretion

The two insulin secreting cell lines, HIT-T15, and βTC-6 (Poitout, V., et al., *Diabetes* (1995) 44:306–313) were purchased from American Type Culture Collection (ATTC) (Manassas, Va., USA). The murine mesangial cell line (SV40 Mes13), and the MDCK cell line were also obtained from ATTC. All cell lines were maintained in culture in ATCC recommended media. The incubation conditions are 37° C., and a constantly circulating mixture of air with 5% carbon dioxide.

In order to avoid interference from the natural insulin secretagogue glucose, the effect of Composition A on insulin secretion was studied under glucose-free conditions. The sulfonylurea compound, tolbutamide was used as the insulin secretagogue in the studies of the effect of Composition A on stimulated insulin secretion.

The cells at about 50–70% confluence were first incubated in glucose-free medium for 2 hours. The medium was then replaced with fresh glucose-free medium and the test extract or fraction was added. The extracts and fractions were always dissolved in dimethyl sulfoxide. The concentration of the stock solution was adjusted always so that addition of 2 μl of stock to 1 ml medium will give the required final concentration. At specific time intervals aliquots of the medium were drawn for the determination of immunoreactive insulin.

Insulin assays were performed using the rat insulin assay kit purchased from Crystal Chemists, Inc. (Chicago, Ill., USA). This kit uses a in an Enzyme Linked Immunosorbent Assay (non-competitive sandwich method). The assay was performed according to the manufacturer's protocol. Briefly, the standard or sample (5 μl) diluted with a sample diluent was added to the wells of a multi-well polystyrene plate. The wells were precoated with antiinsulin antibody. After 2 hours of incubation, the wells were thoroughly washed with a washing buffer. A peroxidase-conjugated antiinsulin antibody solution was then added to the well. After 30 min incubation at room temperature the conjugate solution was removed and the unbound conjugate was washed off. The peroxidase substrate solution (TMB) was then added to the well and the plate was incubated at room temperature for 40 minutes. The enzyme reaction was terminated by the addition of 1N sulfuric acid at the end of this incubation period. The color was read in an microplate reader using a 405 filter.

For testing tolbutamide-induced insulin secretion, the cells were first incubated in glucose-free medium for 2 hours. The medium was then replaced with fresh glucose free medium and various concentrations of the test agent (Composition A or the methanol fraction) was added to the medium. Tolbutamide was then added to a final concentration of 10 μg/ml to βTC-6 cells and 25 μg/ml to HIT-T15 cells. The effect of Composition A on basal insulin secretion in HIT-T15 cells is presented in Table 1.

TABLE 1

Insulin secretion rate is normalized to total cellular protein content of each dish and expressed as ng/ml/mg protein. The differences in values are statistically significant (P < 0.01) for all treatment conditions except for 6.25 μg/ml concentration at 10 and 30-min time points.

| Time after medium replacement | Concentration of Composition A (μg/ml) | | | | |
|---|---|---|---|---|---|
| | 0 | 6.25 | 12.5 | 25 | 50 |
| 10 min. | 0.24 | 0.22 | 0.19 | 0.09 | 0.14 |
| 30 min. | 0.33 | 0.34 | 0.25 | 0.13 | 0.1 |
| 60 min. | 0.37 | 0.28 | 0.21 | | |

The effect of Composition A on basal insulin secretion in βTC-6 cells is shown in FIG. 1. In FIG. 1, βTC-6 cells were grown in 6-well cluster dishes to about 50% confluence and incubated in a glucose-free medium for 2 hours. The medium was replaced by fresh glucose-free medium and Composition A dissolved in 2 μl DMSO was added at various concentrations. Controls contained only 2 μl DMSO. After an hour of incubation with Composition A, the insulin concentration in the medium was determined. As shown, 3.125 μg/ml of Composition A markedly reduced basal insulin secretion from about 1.1 ng/ml/mg protein to only about 0.3 ng/ml/mg protein. Higher concentrations further decreased the secretion in a dose-dependent manner.

For both HIT-T15 cells (Table 1) and βTC-6 cells (FIG. 1) after 2 hours of incubation in the glucose-free medium, the secretion of insulin is steady and Composition A has a potent inhibitory effect on this basal insulin secretion. The inhibitory effect is also broadly linear with respect to dose.

Figure 2:
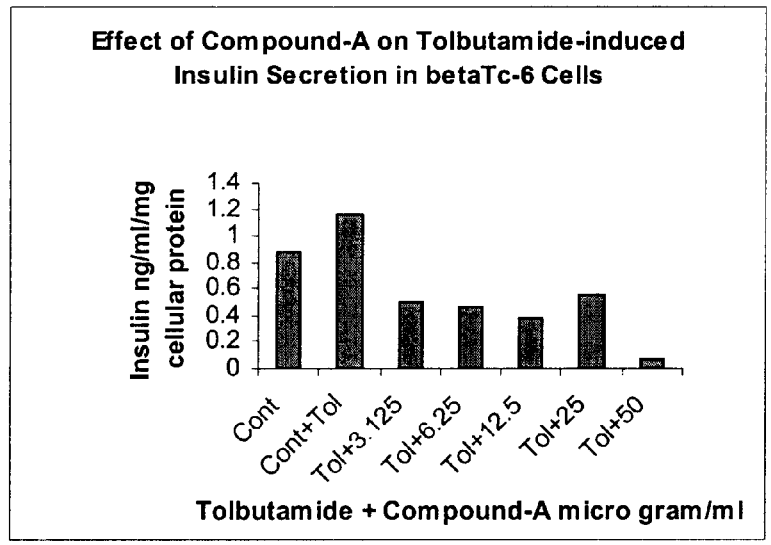
FIG. 2 is a graph showing the effect of Composition A on tolbutamide-induced insulin secretion in βTC-6 cells.
Figure 3:
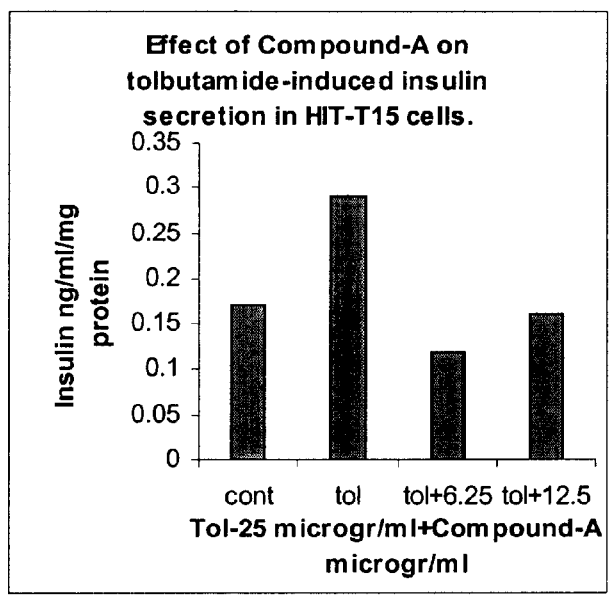
FIG. 3 is a graph showing the effect of Composition A on tolbutamide-induced insulin secretion in HIT-T15 cells.

The effect of Composition A on tolbutamide-induced insulin secretion in HIT-T15 and βTC-6 cells is shown in FIG. 2 and FIG. 3 respectively. The experiments were performed similarly; after 2 hours of glucose deprivation, the medium was replaced with fresh glucose-free medium and Composition A at various concentrations and tolbutamide at 10 μ/ml. Samples were measured 1 hour later. Controls contained 2 μl DMSO.

As shown in FIG. 2, the addition of tolbutamide alone enhanced the production of insulin from 0.9 to 1.2 ng/ml/mg protein; however, addition of various amounts of Composition A decreased secretion; 3.125 μg/ml Composition A decreased production to about 0.5 ng/ml/mg protein. The effect was slightly dose-dependent.

As shown in FIG. 3, tolbutamide increased insulin secretion from about 0.17 ng/ml/mg protein to about 0.3 ng/ml/mg protein. Addition of 6.25 μg/ml of Composition A reduced secretion to 0.13 ng/ml/mg protein; this reduction did not seem to be dose dependent. βTC-6 cell type is much more abundant in insulin; during the 1-hour period following glucose deprivation and replacement of the medium, tolbutamide-treated cells secreted more insulin (approximately 30% more) than the untreated cells.

Composition A significantly inhibited tolbutamide-induced insulin secretion in both these pancreatic β-cells. The cytotoxic effects of Composition A in HIT-T15 cells (shown in Example 3, below) are not evident during the first 1 hour of incubation and therefore decrease in the insulin levels of the medium are not due to cytotoxicity.

Treatment of the cells with Composition A for 1 hour did not permanently damage the cells, because the cells were completely rescued when the cells were transferred to normal growth medium. Composition A was also not cytotoxic at lower concentrations at which it still inhibited insulin secretion. Composition A inhibited basal insulin secretion in the two different pancreatic β-cell lines used here, and potently inhibited tolbutamide-induced insulin secretion in both the cell lines at concentrations as low as 6.25 βg/ml.

Composition A did not have a direct effect on the insulin assay per se. Experiments were conducted to eliminate the possibility that the results are due to Composition A's direct interference with the assay of insulin. For this purpose Composition A dissolved in DMSO (2 μl) was mixed with 1 ml of glucose-free medium at a final concentration of 100 μg/ml. Five μl of this mixture (sham) was added to the well in the ELISA that contained the insulin standard of 6.4 ng/ml. This is the final concentration of Composition A that is present in the insulin assay well when the culture medium from Composition A (at 100 βg/ml)-treated cells is assayed. The insulin ELISA was completed as before and the values obtained for insulin standard and sham-containing insulin standard were compared. Sham did not alter the final readings significantly suggesting that Composition A did not directly influence the insulin assay.

EXAMPLE 3

Cytotoxicity of Composition A

At concentrations of 25 μg/ml and above in two different cell types used in the present studies, Composition A caused lysis and detachment of the cells. To document this property more accurately, cell viability in Composition A-treated cells was determined by two different methods.

In the first method, the cells were grown in 6-well cluster dishes and incubated with Composition A at various concentrations for 4 hours in glucose-free medium. The cell layer was then washed with Hanks Balanced Salt solution (HBSS). The cells that still remained attached to the plate were digested with 1 N sodium hydroxide. The protein content in the digest was determined using a protein assay kit (Pierce, Rockford, Ill., USA). Susceptibility of the cells to Composition A is indicated by low protein content in the treated dishes as compared to controls.

Figure 4:
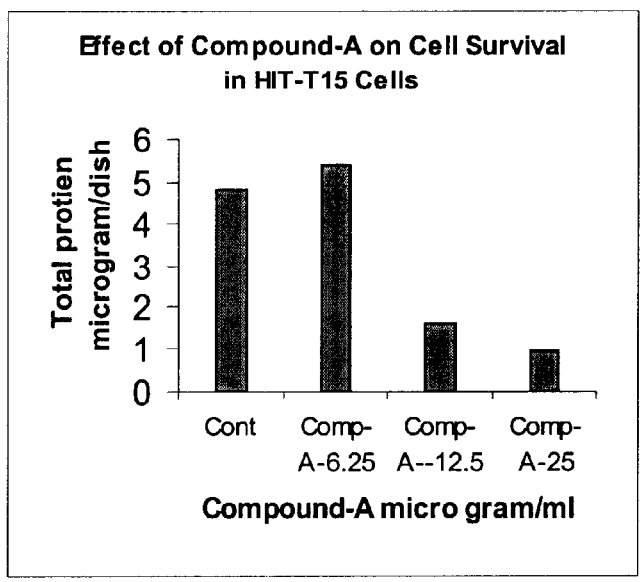
FIG. 4 is a graph showing the cytotoxicity of Composition A on HIT-T15 cells.

The results for HIT-T15 cells are shown in FIG. 4. As shown, the total protein remaining attached to the surface (as indicated by the protein content) in controls is of the order of 5 μg/dish. This is not reduced by 6.25 μg/ml Composition A; however, only 12.5 μg/ml of Composition A lowered the protein levels to about 1.5 μg/dish.

In the second method cells were first treated with Composition A for 24 hours. The cells were then washed with HBSS. The cells that still remained attached were then incubated with 0.4% tryphan blue solution at 37° C. Fifteen minutes later, after a brief wash, the percentage of the cells that absorbed tryphan blue was determined by inspecting under the microscope.

Figure 5:
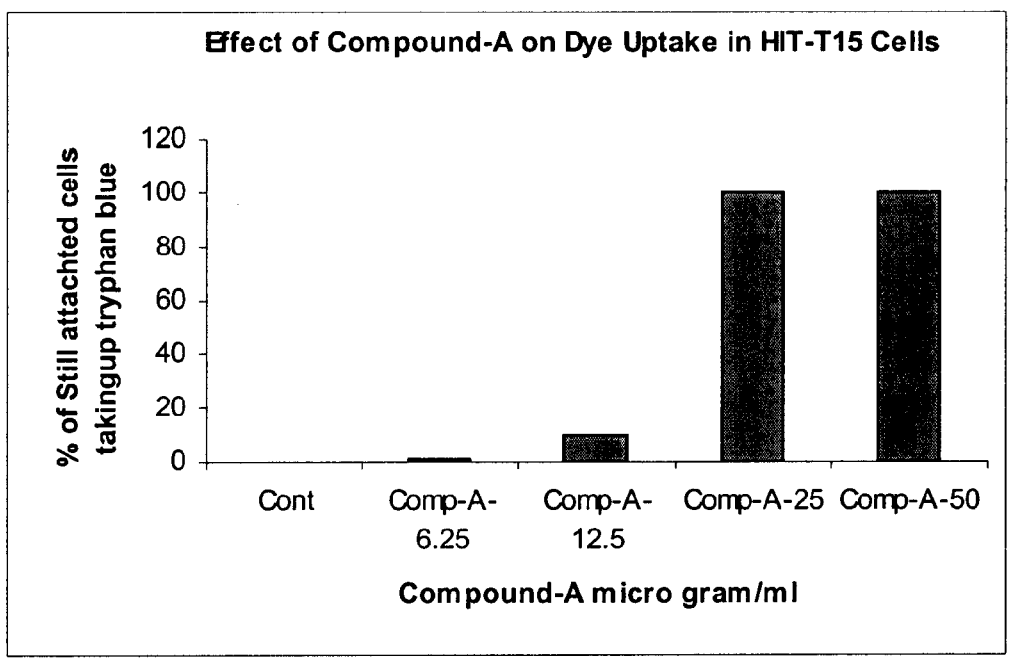
FIG. 5 is a graph showing the cytotoxicity of Composition A as measured by the dye uptake method in HIT-T15 cells.

The results for HIT-T15 cells are shown in FIG. 5. The percentage of cells remaining attached to the dish which take up tryphan blue is undetectable in the control, but the percentage of such cells is 10% when 12.5 μg/ml Composition A is added, and 100% when 25 μg/ml of Composition A is added.

Additional data were obtained when HIT-T15 cells were grown in regular growth medium (RPMI-1640) with 10% fetal bovine serum. In this case, Composition A exhibited a toxic effect only after 18 hours of incubation at 25 μg/ml and above. As shown in FIGS. 4 and 5, Composition A is not cytotoxic at concentration 6.25 μg/ml or less. As shown in Example 2, this concentration, however, inhibits insulin secretion in both HIT-T15 and βTC-6 cells.

Although, as shown above, Composition A is toxic to HIT-T15 cells at concentrations of 12.5 μg/ml and above, βTC-6 cells are resistant to toxicity by Composition A at 100 μg/ml.

It has also been shown that Composition A is cytotoxic to the murine mesangial cell line SV40 Mes13, but not to canine kidney epithelial cells (MDCK).

What is claimed is:

1. A method to isolate a composition which inhibits insulin secretion in βTC-6 cells and HIT-T15 cells and is non-cytotoxic to βTC-6 cells, but cytotoxic to HIT-T15 cells and which is cytotoxic to SV40 Mes13 cells, but not cytotoxic to MDCK cells, which method comprises a) extracting the bark of *Ficus bengalensis* with a solvent consisting of lower alcohols to obtain an extract;

b) drying the extract to obtain a residue;

c) dissolving the residue in methanol;

d) loading the dissolved residue onto an activated silica gel column;

e) eluting the column with a solvent consisting of ethanol:hexane (2:1) to obtain an eluent; and f) removing said solvent from the eluent to obtain said composition.

2. A composition obtainable by the method of claim 1.

* * * * *